Figure 3:
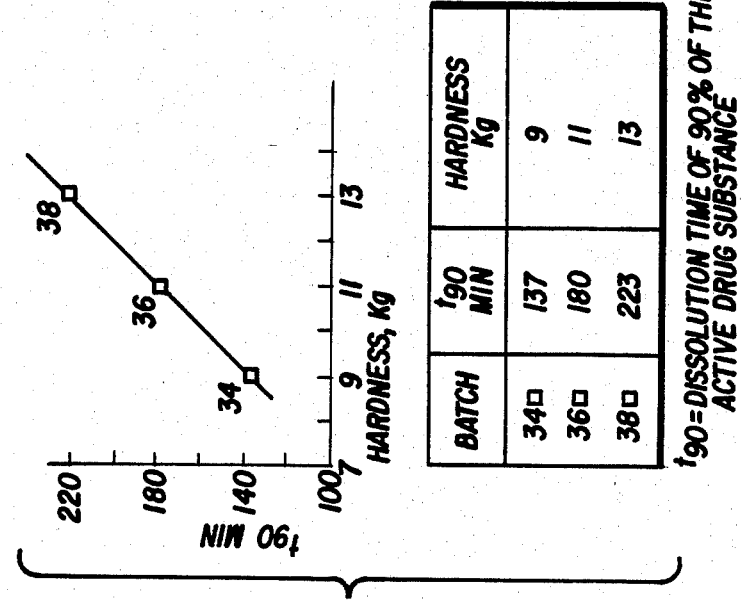

United States Patent [19]

Moro et al.

[11] Patent Number: 4,499,066

[45] Date of Patent: Feb. 12, 1985

[54] PHARMACEUTICAL SUSTAINED-RELEASE COMPOSITIONS

[75] Inventors: Luigi Moro, Cairate; Grazia Maffione, Milan; Guido Neri, Milan; Alessandro Rigamonti, Milan, all of Italy

[73] Assignee: Farmitalia Carlo Erba S.p.A., Milan, Italy

[21] Appl. No.: 403,475

[22] Filed: Jul. 30, 1982

[30] Foreign Application Priority Data

Aug. 5, 1981 [IT] Italy ............................ 23374 A/81

[51] Int. Cl.$^3$ ........................... A61K 9/26; A61K 9/32
[52] U.S. Cl. ........................................ 424/19; 424/22; 424/32; 424/33; 424/81
[58] Field of Search ................... 424/19–22, 424/32, 33, 81

[56] References Cited

U.S. PATENT DOCUMENTS

| Re. 27,107 | 3/1971 | Levesque | 424/22 |
|---|---|---|---|
| 2,987,445 | 6/1961 | Levesque | 424/22 |
| 2,996,431 | 8/1961 | Barry | 424/32 |
| 3,115,441 | 12/1963 | Hermelin | 424/22 |
| 3,317,394 | 5/1967 | Fryklof et al. | 424/22 |
| 3,382,150 | 5/1968 | Grass et al. | 424/33 |
| 3,402,240 | 9/1968 | Cain | 424/22 |
| 3,453,360 | 7/1969 | Hill | 424/33 |
| 3,507,952 | 4/1970 | Rednick | 424/22 |
| 3,908,003 | 9/1975 | Hersh | 424/33 |
| 4,264,573 | 4/1981 | Powell et al. | 424/22 |
| 4,308,251 | 12/1981 | Dunn et al. | 424/22 |
| 4,351,825 | 9/1982 | Sothmann et al. | 424/19 |
| 4,361,545 | 11/1982 | Powell et al. | 424/22 |

OTHER PUBLICATIONS

Ritschel, W. A., Drug Design, vol. IV, Chapter 2, edited by Ariens (Academic Press, N.Y. 1973).
Ballard, B. E., Nelson, E., Chapter 89 in "Remington's Pharmaceutical Sciences", 14th Edition, Mack Publishing Co., Philadelphia 1970.
Baker, R. W., Chapter 2 in "Controlled Release of Biologically Active Agents", edited by Tanquary and Lacey (Plenum Press, N.Y. 1974).
Dakkuri, A., Butler, L. D. and De Luca, P. P., J. Pharm. Sci., 67, 357 (1978).
Itoh, M., Nakano, M., Juni, K. and Sekikawa, H., Chem. Pharm. Bull., 28, 1051 (1980).
Samuelov, Y., Donbrow, M. and Friedman, M., J. Pharm. Sci., 68, 325 (1979).
Buri, P. and Doelker, E., Pharm. Acta Helv., 55, 189 (1980).
Gurny, R., Guitard, P., Buri, P. and Sucker, H., Pharm. Acta Helv., 52, 182 (1977).
Zentner, G. M., Cardinal, J. R. and Sung Wan Kim, J. Pharm. Sci., 67, 1352 (1978).

*Primary Examiner*—Shep K. Rose
*Attorney, Agent, or Firm*—Stevens, Davis, Miller & Mosher

[57] ABSTRACT

New pharmaceutical sustained-release compositions, formulated as tablets, are prepared by mixing the active ingredient with excipient already granulated and coated with polymers and/or copolymers or a polymers- and/or copolymers-mixture substantially insoluble in water. Such pharmaceutical preparations enable one to enhance or to decrease very easily and precisely the sustained-release effect by regulating the granulometry of the excipient, the excipient/active ingredient ratio, the hardness, and the percentage of the polymers and/or copolymers or of the polymers- and/or copolymers-mixture.

10 Claims, 6 Drawing Figures

MODULATION OF THE SUSTAINED RELEASE EFFECT BY VARYING THE TABLET HARDNESS $t_{90}$ = DISSOLUTION TIME OF 90% OF THE ACTIVE DRUG SUBSTANCE

MODULATION OF THE SUSTAINED RELEASE EFFECT WITH RESPECT TO THE VARIATION OF SOME PARAMETERS

MAMMA = METHYLACRYLATE METHYLMETHACRYLATE COPOLYMER
EXCIP. = EXCIPIENT
$t_{50}$ = DISSOLUTION TIME OF 50% OF THE ACTIVE DRUG SUBSTANCE

MODULATION OF THE SUSTAINED RELEASE EFFECT BY VARYING THE QUANTITY OF EXCIPIENT

| BATCH | EXCIPIENT PARTICLE SIZE (mm) | % EXCIP. | $t_{50}$ MIN |
|---|---|---|---|
| 33 o | 0.600 | 63 | 25 |
| 35 o | 0.600 | 67.4 | 27 |
| 37 o | 0.600 | 71 | 57 |
| 34 □ | 0.300 | 63 | 82 |
| 36 □ | 0.300 | 67.4 | 94 |
| 38 □ | 0.300 | 71 | 132 |

EXCIP. = EXCIPIENT $t_{50}$ = DISSOLUTION TIME OF 50% OF THE ACTIVE DRUG SUBSTANCE

KETOPROFEN CONTAINING TABLETS AFTER SEVEN HOURS DISSOLUTION IN SIMULATED PLASMA (9)

DISSOLUTION PLOTS OBTAINED IN A SERIES OF TABLETS WHEREIN ONLY THE ACTIVE INGREDIENT HAS BEEN CHANGED

PHARMACEUTICAL SUSTAINED-RELEASE COMPOSITIONS

DESCRIPTION

The present invention relates to new pharmaceutical sustained-release compositions formulated as tablets, the excipient employed for their preparation, the use of said excipient and of the polymers and/or copolymers employed for its coating in the preparation of said pharmaceutical sustained-release compositions, as well as the process for preparing such pharmaceutical sustained-release compositions.

More particularly, the present invention relates to new pharmaceutical sustained-release compositions, formulated as tablets, characterized in that the active ingredient is mixed in suitable ratios with the excipient already granulated and coated with polymers and/or co-polymers or a mixture of polymers and/or copolymers practically insoluble or only sparingly soluble in aqueous medium.

A further object of the present invention is to provide an excipient for preparing said tablets, characterized in that the excipient is already granulated and coated with polymers and/or copolymers or a mixture of polymers and/or copolymers practically insoluble or sparingly soluble in aqueous medium.

An object of the present invention is also the use of said excipient already granulated and coated with polymers and/or copolymers or a mixture of polymers and/or copolymers substantially insoluble or sparingly soluble in aqueous medium for the preparation of said tablets.

A further object of the present invention is the use of polymers and/or copolymers or a mixture of polymers and/or copolymers substantially insoluble or sparingly soluble in aqueous medium for the preparation of said excipient.

The present invention also comprises preparing the pharmaceutical sustained-release compositions, by mixing the excipient already granulated and coated with polymers and/or copolymers or a mixture of polymers and/or copolymers substantially insoluble or sparingly soluble in aqueous medium, with the active ingredient and, optionally, with flavoring, coloring, sweetening, lubricating and flowing agents, with the thus-obtained mixture being compressed into tablets or compact layers.

In accordance with known techniques in the field of pharmaceutical composition for oral administration, in order to obtain a sustained release of the active ingredient, one skilled in the art may proceed in several ways. For example, the sustained release can be achieved by slackening or reducing the disintegration rate of the drug, for instance, by changing its molecule from a saline to a non-ionized form or by changing the counter-ion of the salt either by acting on the crystalline form or by complexing it.

Furthermore, the sustained release can be obtained by providing a physical barrier between the drug and the dissolution fluids, thus excluding all direct contact. This modus operandi comprises conventional technological processes (for example film-coating, coacervation, micro-encapsulation)—(1) Birrenbach, G. and Speiser, P., J. Pharm. Sci., 65, 1763, (1976)—(2) Marty, J. J., Oppenheim, R. C. and Speiser, P., Pharm. Acta Helv., 53, 17, (1978)—enabling one to coat the active drug substance alone or the pharmaceutical composition "in toto" (for example, tablet, granule, chronoid for slow- and/or timed release) with protective substances.

The sustained release can be also achieved by using relative compression strengths as release-differentiating agent, for example in double-compression tablets or in multilayer tablets—(3) Ritschel, W. A., Drug Design, Vol. IV chap. 2, ed. by Ariens (Academic Press, N.Y., 1973)—(4) Ballard, B. E., Nelson, E., Chapter 89 in "Remington's Pharmaceutical Sciences", 14th ed., Mack Publishing Co., Philadelphia 1970—(5) Baker, R. W., Chapter 2 in "Controlled Release of Biologically Active Agents", ed. by Tanquary and Lacey (Plenum Press., N.Y., 1974).

The technique mostly followed in recent years consists essentially in coating the particles of the active ingredient, both as powder and as finished product, with a film of polymeric pharmacotoxicologically inert substance: by this method the bioavailability of the active ingredient is adjusted by its rate of diffusion through the polymeric barrier—(6) Higuchi, T., J. Pharm. Sci., 52, 1145, (1963)—(7) Desai, S. J., Simonelli, A. P., Higuchi, W. J., J. Pharm. Sci., 55, 1230, (1966). The availability, as liberation of the active ingredient from the pharmaceutical composition proceeds, may not be total in this case and, anyhow, the disadvantage of technical workings involving the active ingredient is remarkable, if one considers process losses and never quantitative yields, besides the requirements to carry out the working on an active ingredient according to the G.M.P. and G.L.P. (Good Manufacturing Practice and Good Laboratories Practice). All this weighs heavily in manufacturing time and costs with marked disadvantages.

Furthermore, it is extremely difficult to achieve smooth formulation patterns and working conditions in order to obtain the sustained release to the required degree. Besides, there always exist problems of probable chemical and/or physical incompatibilities between the active ingredient and the polymers and/or their solvents employed in coating processes.

Now it has been surprisingly found, and this is an important feature of the present invention, that the above disadvantages can be avoided and the sustained release may be readily obtained by new pharmaceutical preparations formulated as tablets, characterized in that the active ingredient is mixed in suitable ratios with the excipient already granulated and coated with polymers and/or copolymers and a mixture of polymers and/or copolymers practically insoluble in aqueous medium.

Preferred polymers and/or copolymers are, for example, polyvinylchloride, polyvinyl alcohol, polyurethane, polytetrafluoroethylene, polystyrene, polysiloxane, polypropylene, polmethyl methacrylate, polylactic acid, polyhydroxyethyl methacrylate, polyglycolic acid, methylacrylate/methylmethacrylate copolymer, polyethylene terephthalate, polyethylene, polyamide, polyacrylonitrile, polycarbonate, polycyanoacrylate, cellulose acetate, and epoxy resins.

Excipients suitable for the preparation of the tablets of the present invention, are for example: calcium phosphate, calcium sulphate, magnesium oxide, lactose, mannitol, maize starch, wheat starch, saccarose, glucose, sorbitol, polyvinylpyrrolidone and substances commercially known as "Emcompress" (Registered Trade-Mark; manufacturer: E. Mendell and Co.), "Elcema" (Registered Trade-Mark; manufacturer: Degussa), "Avicel" (Registered Trade-Mark; manufacturer: FMC Corporation), "Aerosil" (Registered Trade-Mark; manufacturer: Degussa), "Celutab" (Registered Trade-Mark; manufacturer: Mendell), "Methocel" (Registered Trade-Mark; manufacturer: Dow Chemical Co.), "Kollidon" (Registered Trade-Mark; manufacturer: BASF), "Starx" (Registered Trade-Mark; manufacturer: Staley), "Primojel" (Registered Trade-Mark; manufacturer: Scholten), as well as other filler substances usually employed in the preparation of solid pharmaceutical forms which can be obtained by compression.

The coating of these excipients with polymers and/or copolymers or a mixture of polymers and/or copolymers does not adversely affect the main remarkable characteristics of these excipients, as shown by Carr index determinations—(8) Carr, R. L., Brit, Chem. Eng., 15, 1541, (1970)—(showing not only the flowing properties, but also the compressibility characteristics of the granulate), and in fact it even betters them. The results, reported hereinafter in Table 1, obtained by different granulometric classes of a granulate consisting of maize starch-lactose-PVP (ratio 16-8-1), confirm also that after the coating with the methylacrylate/methylmethacrylate copolymer, the flowing and compressibility of the excipient are maintained at very good levels.

The excipient may be either powder alone or granulated mixture.

the formulator's requirements by a suitable choice of the technological conditions and a suitable dosage of the components of the mixture to be compressed.

It is also possible, by a suitable choice of the cited parameters, to prepare non-disintegrating tablets wherein the structural matrix remains unaltered, while still achieving the controlled-release pattern or total drug availability.

Figure 1:
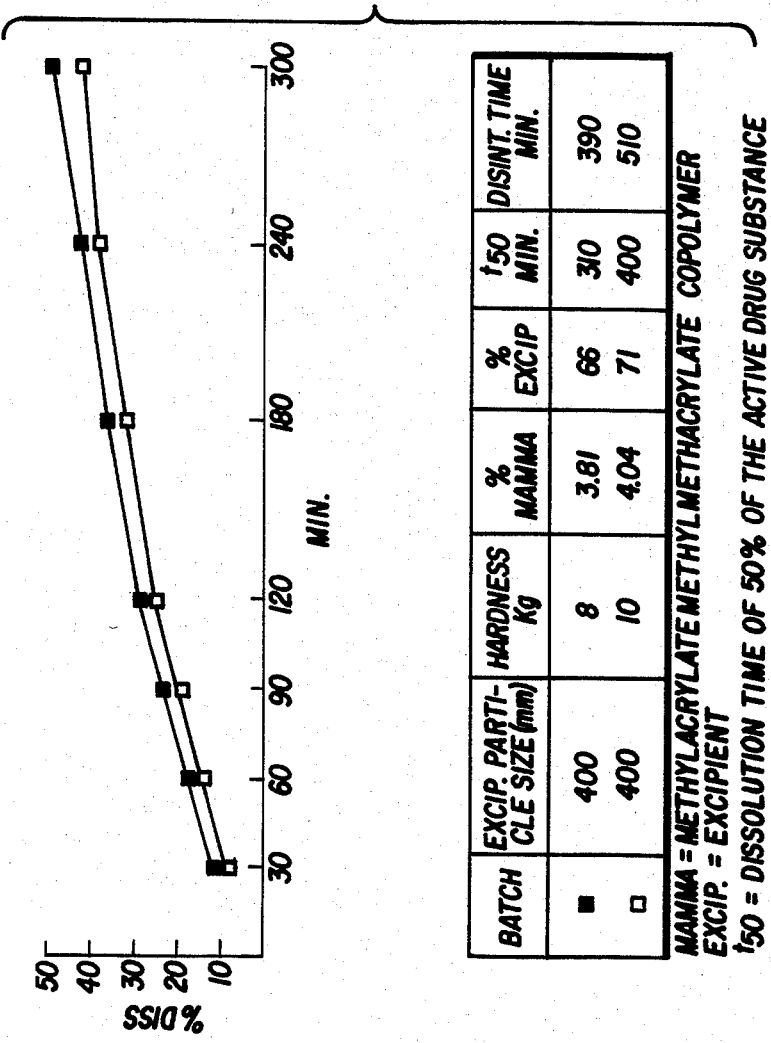

FIG. 1 relates to tablets containing acetylsalicylic acid as active drug substance and shows how it is possible readily to enhance or to decrease the sustained release effect by varying some "parameters".

Figure 2:
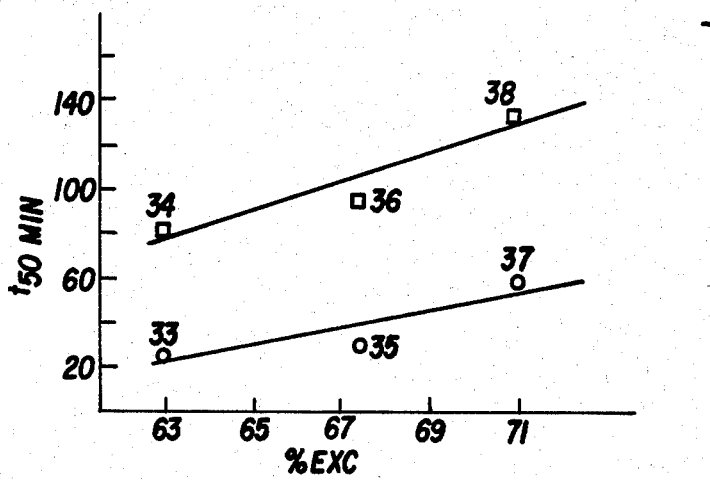

FIG. 2 refers to tablets containing as active ingredient 2-(3-benzoylphenyl)-propionic acid, from now on called Ketoprofen for brevity, and shows how it is possible, by increasing the excipient percentage and decreasing its particle size, to enhance the sustained-release effect.

FIG. 3 relates to tablets containing Ketoprofen as active ingredient and shows how it is possible, by increasing the hardness of the tablet, to enhance the sustained-release effect.

Figure 4:
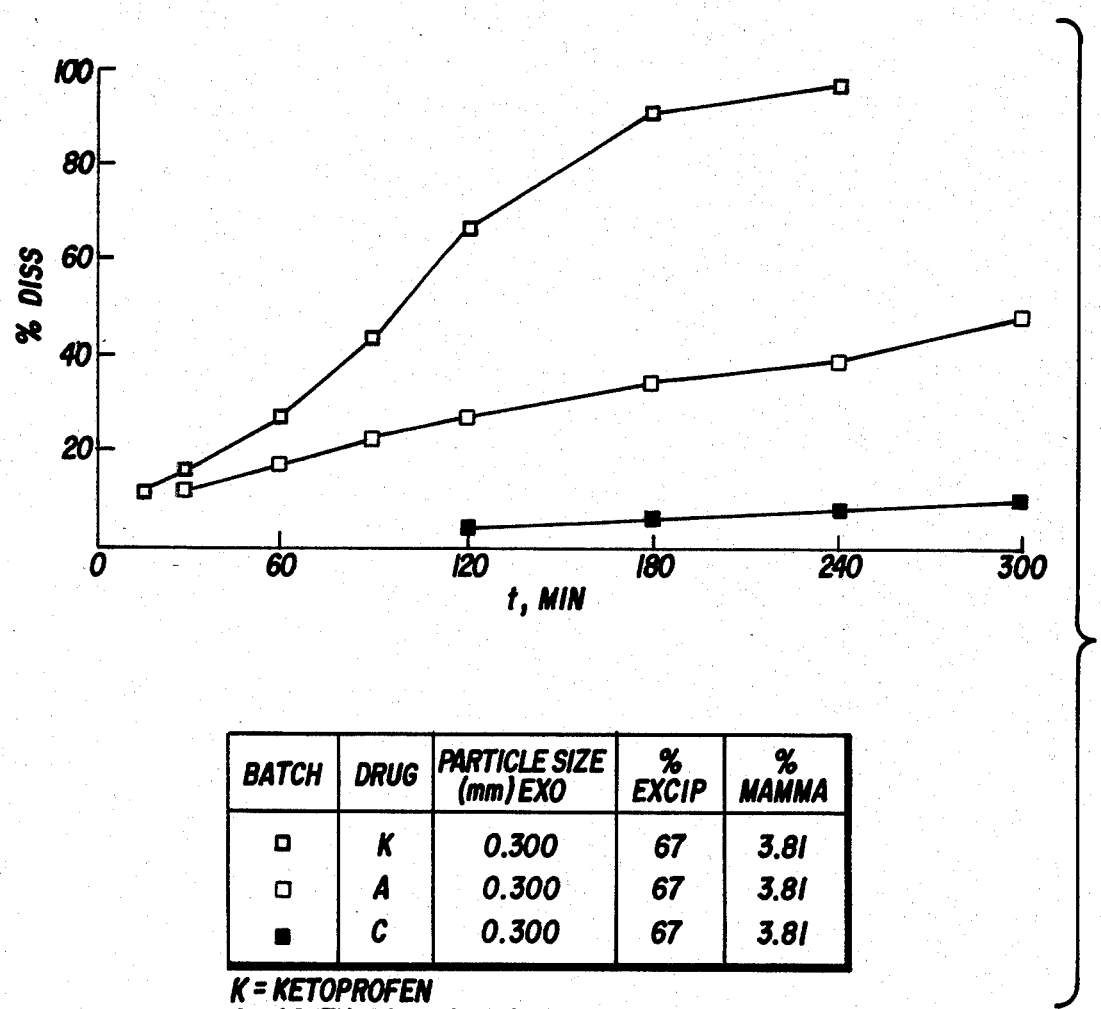

In FIG. 4 it is shown that the sustained-release effect, with the same "parameters", is also due to chemicophysical characteristics of the active ingredient. One can appreciate that different active drug substances, put into otherwise identical formulations, show dissolution

TABLE 1

| Carr index determinations | | | | | | | | |
|---|---|---|---|---|---|---|---|---|
| EXCIPIENT[1] ALONE | | | | COPOLYMER[2] COATED EXCIPIENT[1] | | | | |
| particle size (in mm) | loose bulk density | tapped bulk density | Carr index | particle size (in mm) | % Copolymer coating excipient | loose bulk density | tapped bulk density | Carr index |
| 0.600–0.340 | 0.4124 | 0.4706 | 12.37% | 0.675–0.380 | 6 | 0.4884 | 0.5224 | 11.58% |
| 0.340–0.270 | 0.4082 | 0.4819 | 15.29% | 0.380–0.300 | 4 | 0.4672 | 0.5430 | 13.96% |
| | | | | | 8 | 0.4544 | 0.5190 | 12.45% |
| | | | | | 2 | 0.4709 | 0.540 | 12.80% |
| 0.270–0.225 | 0.4124 | 0.500 | 17.52% | 0.300–0.250 | 6 | 0.4781 | 0.560 | 14.62% |
| | | | | | 10 | 0.4882 | 0.5801 | 15.85% |
| 0.225–0.195 | 0.4167 | 0.5063 | 17.70% | 0.250–0.220 | 4 | 0.4515 | 0.5430 | 16.85% |
| | | | | | 8 | 0.4771 | 0.5779 | 17.44% |
| 0.195–0.170 | 0.4396 | 0.5333 | 17.57% | 0.220–0.195 | 6 | 0.4950 | 0.600 | 17.50% |

[1]EXCIPIENT: maize starch:lactose:pvp (% ratio 64:32:4)
[2]COPOLYMER: methylacrylate/methylmethacrylate copolymer In the compositions there may also be added, in suitable quantities easily determinable by a technician skilled in the art, other substances pharmaceutically acceptable in order to give the tablets particular organoleptic qualities, such as for example flavoring, coloring and sweetening agents, or substances suitable to assist in the manufacturing processes, such as for example lubricating and flowing agents.

The tablets of the present invention have dissolution rates which may vary from a few minutes to several hours by adjusting the different agents that assist in the liberation of the active ingredient from said tablets. Such agents, from now on briefly named "parameters", are the percentage of polymers and/or copolymers coating the excipient, the excipient/active ingredient ratio, the compression strength employed, and the excipient particle size. It is pointed out that, with the same active ingredient, the quality of the excipient to be coated does not at all affect the expected sustained-release effect.

By appropriately adjusting the above cited "parameters", it is extremely simple, and this is a marked advantage of the present invention, to enhance or to decrease the liberation rate of the active ingredient according to rates varying according to the corresponding solubilities in the dissolution medium.

The ranges of the cited "parameters" influencing greatly the achievement of the required sustained release are generally between 0.685 and 0.150 mm, and preferably between 0.380 and 0.220 mm, for the particle size of the excipient; between 0.50% and 50%, and preferably between 1% and 10%, for the amount of coating polymers and/or copolymers; between 0.5 and 25, and preferably between 1 and 10, for the excipient/drug ratio; while the hardness is mostly maintained below 20 kg.

The above mentioned feature of enhancing or decreasing the sustained release effect by adjusting the various "parameters" is a remarkable advantage of the pharmaceutical compositions of the present invention. In fact, for a given active ingredient, by preparing 31 test-formulations and employing the calculation scheme of Cochram-Cox well known to the technician skilled in the art, it is possible to foresee which combinations of the four "parameters" give any desired rate of release, enabling one consequently to choose the most suitable formula for the desired objectives, all with the utmost elasticity and greatest of ease.

This is well illustrated below in Table 2. On the basis of the results of the experimental work described above, four series of values of parameters were selected and the relevant $t_{50\%}$ and $t_{90\%}$ were calculated ($t_{50}$ is the dissolution time of 50% of the active ingredient, and $t_{90}$ is the dissolution time of 90% of the active ingredient). According to the chosen values, 4 batches of tablets were prepared determining the dissolution rates of the active ingredient (Ketoprofen) contained therein. The resulting data show how the predicted values are quite in accordance with the relevant experimental values.

TABLE 2

Results and parameters of check-in formulation

| | PARAMETERS | | | | | | | |
|---|---|---|---|---|---|---|---|---|
| Batch | % Copolymer coating | Excip/drug RATIO | Tablet Hardness (Kg) | Coated Excipient particle size (mm) | Time (min.) | % Dissolved Drug | | |
| | | | | | | Expected | Experimental | Δ% |
| 1 | 6 | 2.5 | 12.5 | 0.675–0.380 | 120 | 90 | 86.98 | 3.35 |
| | | | | | 43 | 50 | 44.80 | 11.1 |
| 2 | 4 | 5 | 15 | 0.250–0.220 | 270 | 90 | 82.0 | 8.8 |
| | | | | | 130 | 50 | 57.0 | 14.8 |
| 3 | 6 | 3.25 | 15 | 0.220–0.195 | 300 | 90 | 79.47 | 11.7 |
| | | | | | 165 | 50 | 52.50 | 5.0 |
| 4 | 6 | 3.5 | 15 | 0.380–0.300 | 300 | 90 | 89.70 | 0.33 |
| | | | | | 136 | 50 | 54.45 | 8.9 |

Figure 5:
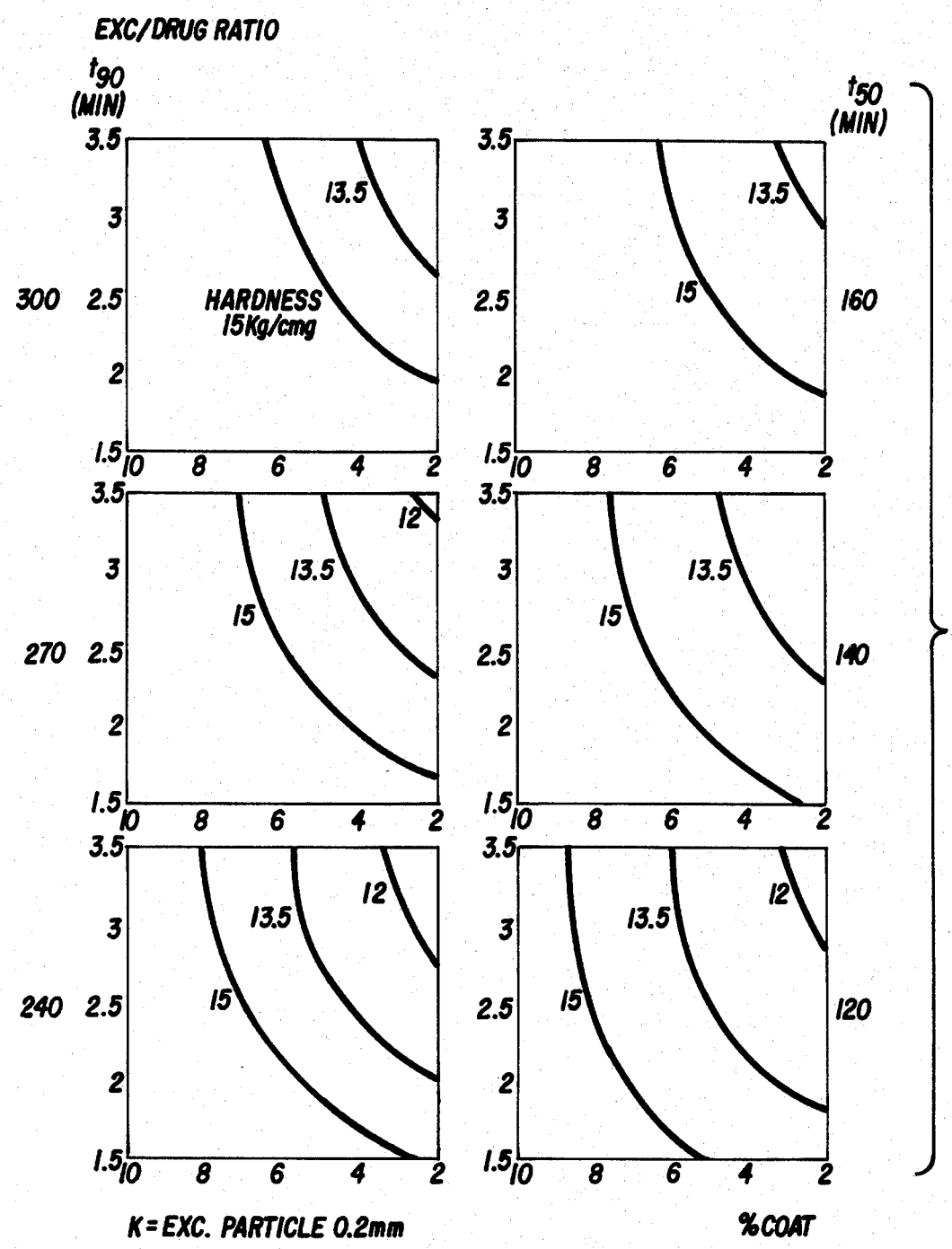

FIG. 5 shows how the values of the "parameters" may be chosen in order to achieve predetermined dissolution rates of the active ingredient. In the ordinates the excipient drug ratios are reported, while in the abscissae the copolymer coating percentage of the excipient is reported, each curve being drawn at constant hardness. The hardness value, in kg, is reported on each curve. All the diagrams of this figure represent a situation in which the particle size "parameter" is kept constant.

Figure 6:
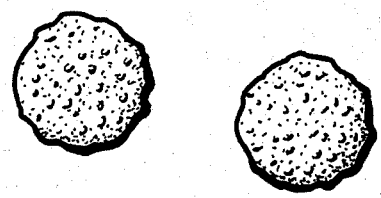

FIG. 6 shows the photographs of some tablets which, even when subjected to dissolution tests until complete drug release occurs, have maintained unaltered their physical structure, turning porous. These are defined herein as non-disintegrating tablets.

The following examples illustrate some preparations according to the present invention, without however limiting it in any way.

In these examples ASA is acetylsalicylic acid; Ketoprofen is 2-(3-benzoylphenyl)propionic acid, Caroxazone is 4H-3-carboxamidomethyl-1,3-benzoxazin-2-one; 4-demethoxydaunomycin hydrochloride is (7S:9S)-9-acetyl-7,8,9,10-tetrahydro-6,7,9,11-tetrahydroxy-7-O-(3'-amino,2',3',6'-trideoxy-α-L-lyxisopyranoside)-5,12-naphthacendione hydrochloride; Indoprofen is 4-(1,3-dihydro-1-oxy-2H-isoindol-2-yl)-α-methylbenzenacetic acid, and MAMMA(°) is methylacrylate/methylmethacrylate copolymer.

The active ingredients have been selected in order to cover a rather large range of solubilities.

EXAMPLE 1

100 g of granulate consisting of 64% lactose, 32% maize starch, 4% polyvinylpyrrolidone, with particle size between 0.340 and 0.270 mm., is suspended in 250 ml of a solution of methylene chloride in which 5 g of MAMMA copolymer were previously dissolved.

The solvent is then evaporated under vacuum till dryness keeping the system under shaking.

The obtained co-precipitate is used as excipient in the preparation of tablets having the following unitary composition:

ASA (micro-encapsulated): 150 mg
Above cited excipient: 330 mg
Mg stearate: 10 mg.

The ingredients are subjected to mixing and then compressed into tablets with a deep concave punch φ 11 mm r 10 (i.e., punch diameter of 11 mm and radius of 10 mm).

Tablets having a hardness of 8 kg were obtained, their rate of disintegration was 6 hours, and the dissolution of the active ingredient reached 50% after 5 hours as indicated below:

| Time (hours) | 1 | 2 | 3 | 4 | 5 |
|---|---|---|---|---|---|
| % of dissolved active ingredient | 18 | 29 | 36 | 42 | 50 |

(°) Registered Trade-Mark: MAMMA resin 100.

EXAMPLE 2

100 g of granulate, consisting of 3 parts of $CaHPO_4 \cdot 2H_2O$ and 1 part of microcrystalline cellulose wet with a few milliliters of a binding solution of polyvinylpyrrolidone, were dried in a fluid bed dryer. Then the granulate, having a particle size between 0.34 and 0.27 mm, was coated with 20 g of PARALOID A 11 copolymer (Registered Trade-Mark; manufacturer Rohm and Haas) dissolved in 100 ml of $CH_2Cl_2$.

The excipient so obtained was utilized to prepare tablets of the following unitary composition:

Ketoprofen: 100 mg
Excipient: 180 mg
Mg stearate: 5.6 mg.

These components were mixed and compressed into tablets with a deep concave punch φ 8 mm r 6 mm.

Tablets were obtained weighing 285 mg and having a hardness of 6 kg and a dissolution of the active ingredient that reached 90% after 3 hours as indicated below:

| Time (minutes) | 15 | 30 | 60 | 90 | 120 | 180 |
|---|---|---|---|---|---|---|
| % of dissolved active ingredient | 12.29 | 34.23 | 46.59 | 58.83 | 75.31 | 89.24 |

The same formula described in this Example 2, but obtained with the excipient not coated with the drug substance copolymer, displayed complete dissolution in less than 20 minutes.

EXAMPLE 3

100 g of granulate consisting of 64% lactose, 34% maize starch, 4% polyvinylpyrrolidone, and having a particle size between 0.380 and 0.300 mm, are suspended in 250 ml of a methylene chloride solution in which 5 g of MAMMA copolymer were previously dissolved. The solvent is evaporated under vacuum till dryness keeping the system under shaking.

A copolymer co-precipitate is obtained on the excipient which is employed in a tablets formulation of the following unitary composition:

Ketoprofen: 150 mg
Excipient: 330 mg
Mg stearate: 10 mg

The components are subjected to mixing and then compressed into tablets with a deep concave punch φ 11 mm r 10 mm.

Tablets have been obtained having a hardness of 8 kg, a disintegration rate of 1.3 hours, and a dissolution of the active ingredient reaching 90% after 3 hours as indicated below:

| Time minutes | 15 | 30 | 60 | 90 | 120 | 180 | 240 |
|---|---|---|---|---|---|---|---|
| % of dissolved active ingredient | 10.08 | 15.46 | 27.87 | 45.95 | 64.41 | 90.11 | 98.48 |

EXAMPLE 4

Operating as previously described, 100 g of granulate consisting of AVICEL PH 102 coated with 6% of MAMMA copolymer in a fluid bed dryer and having a particle size between 0.685 and 0.380 mm, were employed as excipient for a tablet-formulation having the following unitary composition:

Ketoprofen: 150 mg
Excipient: 500 mg
Mg stearate: 13 mg.

Tablets were obtained weighing 663 mg, having a hardness of 6 kg, and a dissolution rate of the active ingredient as indicated below:

| Time (hours) | 1 | 2 | 3 | 4 | 5 |
|---|---|---|---|---|---|
| % of dissolved active ingredient | 34.6 | 55.2 | 76.8 | 94.2 | 98.9 |

EXAMPLE 5

Operating by the same formula as described in Example 4, the compression strength of the tablets was increased so as to obtain tablets having a hardness of 12 Kg.

The relevant dissolution rate of the active ingredient becomes modified consequently as follows:

| Time (hours) | 1 | 2 | 3 | 4 | 5 | 6 |
|---|---|---|---|---|---|---|
| % of dissolved active ingredient | 22.8 | 43.6 | 61.5 | 79.2 | 88.7 | 96.5 |

EXAMPLE 6

100 g of ELCEMA G 250 ® coated with 2% of MAMMA copolymer, and having a particle size between 0.380 and 0.300 mm, were utilized for a tablet formulation having the following unitary composition:

Caroxazone: 100 mg
Excipient: 300 mg
Mg stearate: 8 mg

By compressing the mixture with a flat punch φ 9 mm, tablets were obtained weighing 408 mg, having a hardness of 8 kg, and a dissolution rate of the active ingredient:

| Time (hours) | 1 | 2 | 4 | 6 | 8 | 10 | 12 |
|---|---|---|---|---|---|---|---|
| % of dissolved active ingredient | 8.1 | 17.4 | 29.3 | 38.7 | 47.3 | 60.5 | 73.6 |

EXAMPLE 7

Operating as in the previous examples, 100 g of the excipient lactose coated with 10% PARALOID A 11 (Registered Trade-Mark; manufacturer Rohm and Haas) and having a particle size between 0.300 and 0.250 mm, were employed for a tablet formulation having the following composition:

Ketoprofen: 150 mg
Excipient: 600 mg
Mg stearate: 15 mg.

Tablets were obtained weighing 765 mg, having a hardness of about 6 kg, and a dissolution rate of the active ingredient modified as follows, with respect to the similar tablets of Example 4 and of Example 2:

| Time (hours) | 1 | 2 | 3 | 4 | 5 | 6 |
|---|---|---|---|---|---|---|
| % of dissolved active ingredient | 12 | 29 | 51 | 74 | 91 | 98 |

EXAMPLE 8

1 kg of lactose with particle size between 0.250 and 0.220 mm was put into a pan-coat and coated by spraying 500 ml of an 8% MAMMA solution. By employing this excipient, the following tablet formulation was prepared.

Indoprofen: 150 mg
Excipient: 450 mg
Mg stearate: 12 mg.

The tablets so obtained, each weighing 612 mg and having a 12 kg hardness, displayed the dissolution rate of the active ingredient reported below:

| Time (minutes) | 60 | 84 | 115 | 180 | 290 | 395 | 560 | 750 |
|---|---|---|---|---|---|---|---|---|
| % of dissolved active ingredient | 20 | 30 | 40 | 50 | 60 | 70 | 80 | 90 |

EXAMPLE 9

Operating as in Example 8, a tablet-formulation was prepared differing from that of the previous example as to the particle size of the excipient: in fact, lactose was employed having a particle size between 0.380 and 0.300 mm.

The dissolution rate of the active ingredient was as follows:

| Time (minutes) | 21 | 45 | 75 | 105 | 140 | 185 | 245 | 287 |
|---|---|---|---|---|---|---|---|---|
| % of dissolved active ingredient | 20 | 30 | 40 | 50 | 60 | 70 | 80 | 90 |

EXAMPLE 10

By using the same granulate as in Example 1 (coated however with 4.04% of MAMMA), tablets were prepared having the following composition:
ASA: 150 mg
Excipient: 399 mg
Mg stearate: 11 mg.

At a hardness of 10 kg, a disintegration time of 510 minutes resulted and the dissolution rate of the active ingredient was:

| Time (minutes) | 35 | 94 | 162 | 264 |
|---|---|---|---|---|
| % of dissolved active ingredient | 10 | 20 | 30 | 40 |

EXAMPLE 11

100 g of mannitol are put into a fluid bed dryer and coated with 4 g of methylacrylate/methylmethacrylate copolymer (MAMMA) in aqueous emulsion.

The excipient thus coated was then sifted and the fraction isolated having a particle size between 0.300 and 0.250 mm. The latter was employed to prepare tablets having the following unitary composition:
4-demethoxydaunomycin.HCl: 10 mg
Excipient: 80 mg
Mg stearate: 1.8 mg.

These components, after appropriate mixing, were compressed into tablets with a deep concave punch $\phi$ 5 mm r 3.5 mm.

Tablets were obtained weighing 91.8 mg, having a hardness of 5 kg, and a dissolution of the active ingredient as reported below:

| Time (hours) | 1 | 2 | 4 | 6 | 8 | 12 |
|---|---|---|---|---|---|---|
| % of dissolved active ingredient | 11.3 | 18.5 | 27.1 | 46.4 | 60.9 | 78.4 |

EXAMPLE 12

Operating as in the previous example, 100 g of mannitol were coated with 6% of MAMMA resin 100 ® and suitably sifted to a particle size ranging between 0.25 and 0.22 mm. The resulting excipient was then utilized to prepare implantology device tablets of the following unitary composition:
4-demethoxydaunomycin.HCl: 8 mg
Excipient: 80 mg
Mg stearate: 1.7 mg.

These components, after mixing, were compressed into tablets with a flat $\phi$ 5 mm punch.

Tablets were thus obtained weighing 89.7 mg, having a hardness of 10 kg, and a very low dissolution rate of the active ingredient, as reported below:

| Time (days) | 2 | 3 | 4 | 5 | 6 | 8 |
|---|---|---|---|---|---|---|
| % of dissolved active ingredient | 23 | 37 | 48 | 56 | 64 | 76 |

What is claimed is:

1. A process for preparing a pharmaceutical sustained-release composition formulated as tablets, comprising:
   coating particles of an excipient selected from the group consisting of starch, lactose, mannitol, saccarose, glucose, and sorbitol with a polymeric material selected from the group consisting of acrylate polymers and methacrylate polymers and copolymers to form coated granules of the excipient, said polymeric material being substantially insoluble or sparingly soluble in aqueous medium;
   mixing an uncoated active ingredient with the coated granules of the excipient and
   compressing the mixture to form tablets having a hardness in the range of from at least 5 kg to less than 20 kg.

2. A pharmaceutical sustained-release composition formulated as tablets having a hardness in the range of from about 5 kg to less than 20 kg prepared by the process of claim 1, said composition comprising an uncoated active ingredient admixed with a granulated excipient selected from the group consisting of starch, lactose, mannitol, saccarose, glucose and sorbitol that has been previously coated with 0.5 to 50% by weight based on the weight of the excipient of a polymeric material selected from the group consisting of acrylate polymers and methacrylate polymers and copolymers, the ratio by weight of the excipient to the active ingredient being in the range of 0.5 to 25.

3. The composition of claim 2, wherein the excipient is coated with 1 to 10% or more by weight of the polymeric material.

4. The composition of claim 2, wherein the ratio by weight of the coated excipient to the active ingredient is in the range of 1 to 10.

5. The composition of claim 2, wherein the particle size of the excipient is in the range of 0.150 mm to 0.685 mm.

6. The composition of claim 5, wherein the particle size of the excipient is in the range of 0.220 to 0.380 mm.

7. The composition of claim 2, wherein the particle size of the excipient is in the range of 0.220 to 0.380 mm, the excipient is coated with 1 to 10% or more by weight of the polymeric material, and the ratio by weight of the coated excipient to the active ingredient is in the range of 1 to 10.

8. A pharmaceutical composition as defined in claim 2, characterized in that the polymeric material comprises methylacrylate/methylmethacrylate copolymer.

9. A process as defined in claim 1, characterized in that the polymeric material comprises methylacrylate/methylmethacrylate copolymer.

10. A pharmaceutical composition as defined in any one of claims 8 and 2 to 7, characterized in that the tablets do not disintegrate, but nevertheless allow substantially total drug release.

* * * * *

UNITED STATES PATENT AND TRADEMARK OFFICE
CERTIFICATE OF CORRECTION

PATENT NO. : 4,499,066
DATED : February 12, 1985
INVENTOR(S) : MORO et al.

It is certified that error appears in the above-identified patent and that said Letters Patent is hereby corrected as shown below:

FIG. 4: in the third column of the Table "Particle size (mm) EXO" should read --Particle Size (mm) EXC --.

FIG. 5: in the first graph, "Hardness 15KG/cmg" should read --Hardness 15Kg -- ;

FIG 5: at the end of the page "K=Exc. Particle 0.2mm" should read --K=Exc.Particle Size 0.2mm--.

Column 6, line 36, the expression:
"Registered Trade-Mark: MAMMA resin 100" should be placed at the end of column 5 or, always at column 5, before EXAMPLE 1.

Signed and Sealed this

Twenty-seventh Day of August 1985

[SEAL]

Attest:

DONALD J. QUIGG

Attesting Officer     Acting Commissioner of Patents and Trademarks